United States Patent
Cho et al.

(10) Patent No.: US 10,426,543 B2
(45) Date of Patent: Oct. 1, 2019

(54) KNIFE TRIGGER FOR VESSEL SEALER

(71) Applicant: COVIDIEN LP, Mansfield, MA (US)

(72) Inventors: Hoon Cho, Seoul (KR); Seokjoo Chang, Seoul (KR)

(73) Assignee: COVIDIEN LP, Mansfield, MA (US)

( * ) Notice: Subject to any disclaimer, the term of this patent is extended or adjusted under 35 U.S.C. 154(b) by 809 days.

(21) Appl. No.: 15/004,919

(22) Filed: Jan. 23, 2016

(65) Prior Publication Data

US 2017/0209205 A1    Jul. 27, 2017

(51) Int. Cl.
*A61B 18/14* (2006.01)
*A61B 18/00* (2006.01)
(Continued)

(52) U.S. Cl.
CPC ...... *A61B 18/1445* (2013.01); *A61B 18/1206* (2013.01); *A61B 2017/2919* (2013.01); *A61B 2017/2939* (2013.01); *A61B 2018/0063* (2013.01); *A61B 2018/126* (2013.01); *A61B 2018/1455* (2013.01)

(58) Field of Classification Search
CPC .... A61B 2018/1455; A61B 2017/2912; A61B 2017/2919; A61B 2017/2922; A61B 2017/2939; A61B 2017/2941; A61B 17/2909; A61B 2017/291–2925; A61B 2017/2932–2941; A61B 18/1442–1447; A61B 2018/145–1457
See application file for complete search history.

(56) References Cited

U.S. PATENT DOCUMENTS

D249,549 S   9/1978   Pike
D263,020 S   2/1982   Rau, III
(Continued)

FOREIGN PATENT DOCUMENTS

CN   201299462     9/2009
CN   202086577 U   12/2011
(Continued)

OTHER PUBLICATIONS

Seyfan et al. "Sutureless Closed Hemontoidectomy: A New Technique" Annals of Surgery vol. 234 No. 1, Jul. 2001 pp. 21-24.
(Continued)

*Primary Examiner* — Jaymi E Della
*Assistant Examiner* — Sean W Collins

(57) ABSTRACT

A forceps includes at least one shaft and a housing defining a cavity. An end effector assembly is attached to the shaft(s) and includes first and second jaw members movable relative to one another from a spaced apart position to a closer position. A knife channel defined within the jaw members is configured to receive a knife. A trigger assembly is disposed within the cavity and includes a trigger having a first link pivotably coupled at one end to the trigger and slidingly engaged to a second link at the other end. The second link includes a first end telescopically slideable relative to the first link upon actuation of the trigger through a range of motion and a second end pivotably coupled to a third link which, in turn, couples to the knife. Actuation of the trigger translates the knife through the knife channel.

14 Claims, 5 Drawing Sheets

(51) Int. Cl.
  *A61B 18/12* (2006.01)
  *A61B 17/29* (2006.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,100,420 A | 3/1992 | Green et al. |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,578,052 A | 11/1996 | Koros et al. |
| 5,618,294 A | 4/1997 | Aust et al. |
| D384,413 S | 9/1997 | Zlock et al. |
| 5,665,100 A | 9/1997 | Yoon |
| H1745 H | 8/1998 | Paraschac |
| 5,814,043 A | 9/1998 | Shapeton |
| 5,827,279 A | 10/1998 | Hughett et al. |
| D402,028 S | 12/1998 | Grimm et al. |
| D408,018 S | 4/1999 | McNaughton |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H1904 H | 10/2000 | Yates et al. |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossein et al. |
| H2037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,673,092 B1 | 1/2004 | Becher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture et al. |
| 7,101,371 B2 | 9/2006 | Dycus et al. |
| D531,311 S | 10/2006 | Guerra et al. |
| 7,118,570 B2 | 10/2006 | Tetzlaff et al. |
| 7,131,970 B2 | 11/2006 | Moses et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,252,667 B2 | 8/2007 | Moses et al. |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| 7,922,718 B2 | 4/2011 | Moses et al. |
| 8,070,748 B2 | 12/2011 | Hixson et al. |
| 8,092,451 B2 | 1/2012 | Schechter et al. |
| 8,112,871 B2 | 2/2012 | Brandt et al. |
| 8,133,254 B2 | 3/2012 | Dumbauld et al. |
| 8,147,489 B2 | 4/2012 | Moses et al. |
| 8,162,965 B2 | 4/2012 | Reschke et al. |
| 8,187,273 B2 | 5/2012 | Kerr et al. |
| 8,215,182 B2 | 7/2012 | Artale et al. |
| 8,257,352 B2 | 9/2012 | Lawes et al. |
| 8,266,783 B2 | 9/2012 | Brandt et al. |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,298,233 B2 | 10/2012 | Mueller |
| 8,323,310 B2 | 12/2012 | Kingsley |
| 8,343,150 B2 | 1/2013 | Artale |
| 8,343,151 B2 | 1/2013 | Siebrecht et al. |
| 8,348,948 B2 | 1/2013 | Bahney |
| 8,357,159 B2 | 1/2013 | Romero |
| 8,388,647 B2 | 3/2013 | Nau, Jr. et al. |
| 8,394,096 B2 | 3/2013 | Moses et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,512,371 B2 | 8/2013 | Kerr et al. |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,568,412 B2 | 10/2013 | Brandt et al. |
| 8,585,736 B2 | 11/2013 | Horner et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,641,713 B2 | 2/2014 | Johnson et al. |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,115 B2 | 3/2014 | Reschke |
| 8,685,009 B2 | 4/2014 | Chernov et al. |
| 8,685,021 B2 | 4/2014 | Chernov et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |

(56) References Cited

U.S. PATENT DOCUMENTS

| | | |
|---|---|---|
| 8,840,639 B2 | 9/2014 | Gerhardt, Jr. et al. |
| 8,852,185 B2 | 10/2014 | Twomey |
| 8,858,553 B2 | 10/2014 | Chojin |
| 8,888,771 B2 | 11/2014 | Twomey |
| 8,888,775 B2 | 11/2014 | Nau, Jr. et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,125 B2 | 2/2015 | Schechter et al. |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,358 B2 | 3/2015 | Reschke |
| 8,968,359 B2 | 3/2015 | Kerr et al. |
| 9,005,200 B2 | 4/2015 | Roy et al. |
| 9,017,372 B2 | 4/2015 | Artale et al. |
| 9,024,237 B2 | 5/2015 | Bonn |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,060,798 B2 | 6/2015 | Harper et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,192,430 B2 | 11/2015 | Rachlin et al. |
| 9,265,568 B2 | 2/2016 | Chernov et al. |
| 2003/0018332 A1 | 1/2003 | Schmaltz et al. |
| 2003/0109875 A1 | 6/2003 | Tetzlaff et al. |
| 2003/0229344 A1 | 12/2003 | Dycus et al. |
| 2004/0092927 A1 | 5/2004 | Podhajsky et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2006/0074417 A1 | 4/2006 | Cunningham et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0260241 A1 | 11/2007 | Dalla Betta et al. |
| 2008/0215048 A1 | 9/2008 | Hafner et al. |
| 2008/0300613 A1 | 12/2008 | Shelton, IV et al. |
| 2009/0012520 A1 | 1/2009 | Hixson et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2010/0016857 A1 | 1/2010 | McKenna et al. |
| 2010/0130977 A1 | 5/2010 | Garrison et al. |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0228250 A1 | 9/2010 | Brogna |
| 2010/0249769 A1 | 9/2010 | Nau, Jr. et al. |
| 2010/0249776 A1 | 9/2010 | Kerr |
| 2010/0274244 A1 | 10/2010 | Heard |
| 2010/0292691 A1 | 11/2010 | Brogna |
| 2010/0305567 A1 | 12/2010 | Swanson |
| 2011/0054468 A1 | 3/2011 | Dycus |
| 2011/0054471 A1 | 3/2011 | Gerhardt et al. |
| 2011/0060335 A1 | 3/2011 | Harper et al. |
| 2011/0060356 A1 | 3/2011 | Reschke et al. |
| 2011/0071523 A1 | 3/2011 | Dickhans |
| 2011/0072638 A1 | 3/2011 | Brandt et al. |
| 2011/0077648 A1 | 3/2011 | Lee et al. |
| 2011/0087218 A1 | 4/2011 | Boudreaux et al. |
| 2011/0193608 A1 | 8/2011 | Krapohl |
| 2011/0218530 A1 | 9/2011 | Reschke |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059375 A1 | 3/2012 | Couture et al. |
| 2012/0059409 A1 | 3/2012 | Reschke et al. |
| 2012/0083786 A1 | 4/2012 | Artale et al. |
| 2012/0083827 A1 | 4/2012 | Artale et al. |
| 2012/0123404 A1 | 5/2012 | Craig |
| 2012/0123410 A1 | 5/2012 | Craig |
| 2012/0130367 A1 | 5/2012 | Garrison |
| 2012/0172868 A1 | 7/2012 | Twomey et al. |
| 2012/0172873 A1 | 7/2012 | Artale et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296323 A1 | 11/2012 | Chernov et al. |
| 2012/0316601 A1* | 12/2012 | Twomey ............ A61B 18/1445 606/205 |
| 2012/0323238 A1 | 12/2012 | Tyrrell et al. |
| 2012/0330308 A1 | 12/2012 | Joseph |
| 2013/0018364 A1 | 1/2013 | Chernov et al. |
| 2013/0022495 A1 | 1/2013 | Allen, IV et al. |
| 2014/0135758 A1 | 5/2014 | Mueller |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 1532932 A1 | 5/2005 |
| EP | 1609430 A1 | 12/2005 |
| EP | 1810625 A1 | 7/2007 |
| EP | 2353535 A1 | 8/2011 |
| EP | 2436330 A1 | 4/2012 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 08056955 | 3/1996 |
| JP | 08252263 A | 10/1996 |
| JP | 8-317934 A | 12/1996 |
| JP | 09010223 | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |

(56) References Cited

FOREIGN PATENT DOCUMENTS

| | | |
|---|---|---|
| JP | 2000342599 A | 12/2000 |
| JP | 2000350732 A | 12/2000 |
| JP | 2001-8944 | 1/2001 |
| JP | 2001008944 A | 1/2001 |
| JP | 2001029356 A | 2/2001 |
| JP | 2001128990 A | 5/2001 |
| JP | 2001-190564 A | 7/2001 |
| JP | 2004-517668 A | 6/2004 |
| JP | 2004-528869 A | 9/2004 |
| SU | 401367 A1 | 10/1973 |
| WO | 94/00059 | 1/1994 |
| WO | 99-23933 A2 | 5/1999 |
| WO | 00/24330 | 5/2000 |
| WO | 0036986 A1 | 6/2000 |
| WO | 0115614 A1 | 3/2001 |
| WO | 0154604 A1 | 8/2001 |
| WO | 02/080793 | 10/2002 |
| WO | 2005/110264 A2 | 11/2005 |
| WO | 2015017994 A1 | 2/2015 |

OTHER PUBLICATIONS

Craig Johnson. "Use of the LigaSure Vessel Sealing System in Bloodless Hemorrhoidectomy" That Work, Mar. 2000.
Jarrett et al., "Use of the LigaSure Vessel Sealing System for Perl-Hilar Vessels in Laparoscopic Nephrectomy" Sales Product Literature.
US. Appl. No. 09/387,883, filed Sep. 1, 1999.
U.S. Appl. No. 09/591,328, filed Jun. 9, 2000.
U.S. Appl. No. 12/336,970, filed Dec. 17, 2008.
Peterson et al. "Comparison of Healing Process Following Ligation with Sutures and Bipolar Vessel Sealing" Surgical Technology International (2001).
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Nashington University School of Medicine, St. Louis MO, Presented at AHPBA, Feb. 2001.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 06005185.1 dated May 10, 2006.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale R. Schmaltz.
U.S. Appl. No. 12/336,970, filed Dec. 17, 2008, Paul R. Sremeich.
Michael Choti, "Abdominoperineal Resection with the LigaSure Vessel Sealing System and LigaSure Atlas 20 cm Open Instrument" Innovations That Work, .quadrature.Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

(56) References Cited

OTHER PUBLICATIONS

"Electrosurgery: A Historical Overview" Innovations in Electrosurgery; Sales/Product Literature; Dec. 31, 2000.
Muller et al., "Extended Left Hemicoletomy Using the LigaSure Vessel Sealing System" Innovations That Work,. quadrature.Sep. 1999.
Carus et al., "Initial Experience With the LigaSure Vessel Sealing System in Abdominal Surgery" Innovations That Work,.quadrature. Jun. 2002.
Paul G. Horgan, "A Novel Technique for Parenchymal Division During Hepatectomy" The American Journal of Surgery vol. 181, No. 3, Apr. 2001 pp. 236-237.
Olsson et al. "Radical Cystectomy in Females" Current Surgical Techniques in Urology, vol. 14, Issue 3.

\* cited by examiner

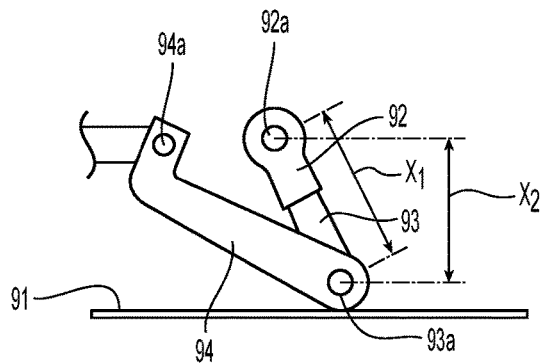
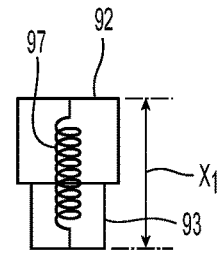
Fig. 4A          Fig. 4B
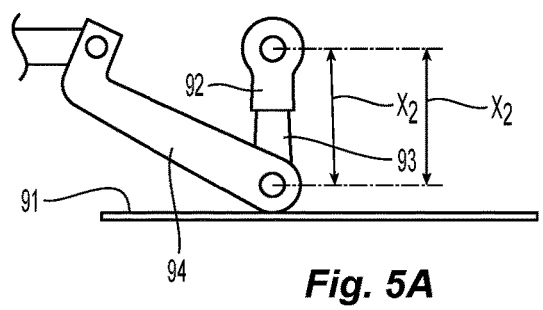
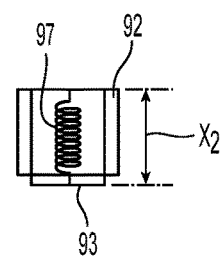
Fig. 5A          Fig. 5B
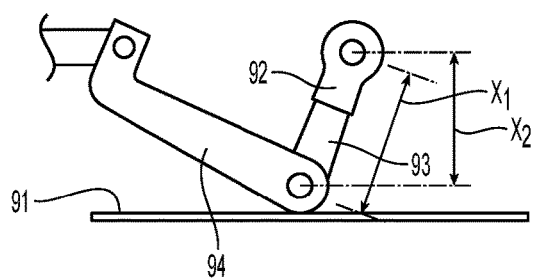
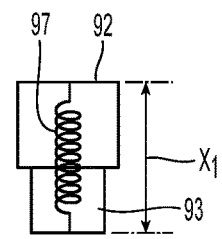
Fig. 6A          Fig. 6B

KNIFE TRIGGER FOR VESSEL SEALER

BACKGROUND

1. Background of Related Art

The present disclosure relates to forceps used for open surgical procedures. More particularly, the present disclosure relates to an open bipolar forceps that is capable of sealing and cutting tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue to create a tissue seal. Once sealed, a knife may be advanced through the tissue seal to cut the tissue using a knife trigger.

SUMMARY

The present disclosure relates to forceps used for surgical procedures. More particularly, the present disclosure relates to a bipolar forceps for treating tissue that is capable of sealing and cutting tissue.

As is traditional, the term "distal" refers herein to an end of the apparatus that is farther from an operator, and the term "proximal" refers herein to the end of the electrosurgical forceps that is closer to the operator.

Aspects of the present disclosure include a bipolar forceps having one or more members and a housing defining a cavity disposed on the one or more shaft members. An end effector assembly is attached the shaft member(s) and includes first and second jaw members that are movable relative to one another a pivot from a spaced apart position to a position closer to one another. A knife channel is defined within the jaw members and is configured to receive a knife therethrough. A trigger assembly is disposed within the cavity and includes a trigger having a first link pivotably coupled at one end to the trigger and slidingly engaged to a second link at the other end. A second link includes a first end that is slidingly receivable within the first link upon actuation of the trigger through a range of motion and a second end pivotably coupled to a third link which, in turn, couples to the knife. Actuation of the trigger translates the knife through the knife channel through the range of motion.

In one aspect, the first and second links are transitionable through the range of motion of the trigger from an extended configuration wherein the length of the first and second links combines to a first length to a compressed configuration wherein the length of the first and second links combines to a second length. The second length is shorter than the first length. The second link may be telescopically received within the first link or voce versa.

In other aspects, a biasing member is disposed within one or both of the first and second links and is configured to bias the links in the extended configuration. In yet other aspects, the first and second links transition between the extended and compressed configurations through the range of motion of the trigger during actuation and release. In still other aspects, the first and second links are normal to one another when disposed in the compressed configuration.

In aspects, the transitioning of the first and second links through the range of motion of the trigger from the extended configuration to the compressed configuration reduces an arc of rotation of the trigger, which, in turn, reduces the necessary size of the cavity.

In aspects, the pivot defines a longitudinal slot therethrough and the knife is configured to move within the longitudinal slot upon translation thereof.

The present disclosure also relates to a bipolar forceps including first and second shaft members. One (or both) of the first and second shaft members is configured to support a housing defining a cavity therein. A first jaw member is attached to the first shaft member and a second jaw member attached to the second shaft member. The jaw members are movable relative to one another about a pivot from a spaced apart position to a position closer to one another. One (or both) of the jaw members includes a knife channel defined therein which is configured to receive a knife therethrough. A trigger assembly is disposed within (or partially disposed within) the cavity and includes a trigger having a first link pivotably coupled at one end thereto and slidingly engaged to a second link at the other end thereof. The second link includes a first end that is slidingly receivable within (or at least partially within) the first link (or vice versa) upon actuation of the trigger through a range of motion and a second end that is pivotably coupled to a third link which, in turn, couples to the knife such that actuation of the trigger translates the knife through the knife channel through the range of motion.

In aspects, the links are transitionable through the range of motion of the trigger from an extended configuration wherein the length of the first and second links combines to a first length to a compressed configuration wherein the length of the first and second links combines to a second length, the second length being shorter than the first length. A biasing member is disposed within at least one of the first and second links and is configured to bias the links in the extended configuration. In aspects, the second link is telescopically received within the first link (or vice versa).

In other aspects, the first and second links transition between the extended and compressed configurations through the range of motion of the trigger during actuation and release. In yet other aspects, the first and second links are normal to the third link when disposed in the compressed configuration or fully compressed configuration. The transitioning of the first and second links through the range of motion of the trigger from the extended configuration to the compressed configuration reduces an arc of rotation of the trigger, which, in turn, reduces the necessary size of the cavity.

In still other aspects, the pivot defines a longitudinal slot therethrough and the knife is configured to advance through the longitudinal slot upon translation thereof.

BRIEF DESCRIPTION OF THE DRAWINGS

Various embodiments of the bipolar forceps are described herein with reference to the drawings wherein:

FIG. 4A is an enlarged, side view of various linkages of the trigger assembly shown in the unactuated position;

FIG. 4B is as internal, schematic view of a compression spring of the trigger assembly shown in an extended orientation;

FIG. 5A is an enlarged, side view of the various linkages of the trigger assembly shown in a compressed orientation;

FIG. 5B is as internal, schematic view of the compression spring of the trigger assembly shown in the compressed orientation;

FIG. 6A is an enlarged, side view of the various linkages of the trigger assembly shown in a second extended orientation;

FIG. 6B is as internal, schematic view of the compression spring the trigger assembly shown in the second extended orientation.

DETAILED DESCRIPTION

Figure 1:
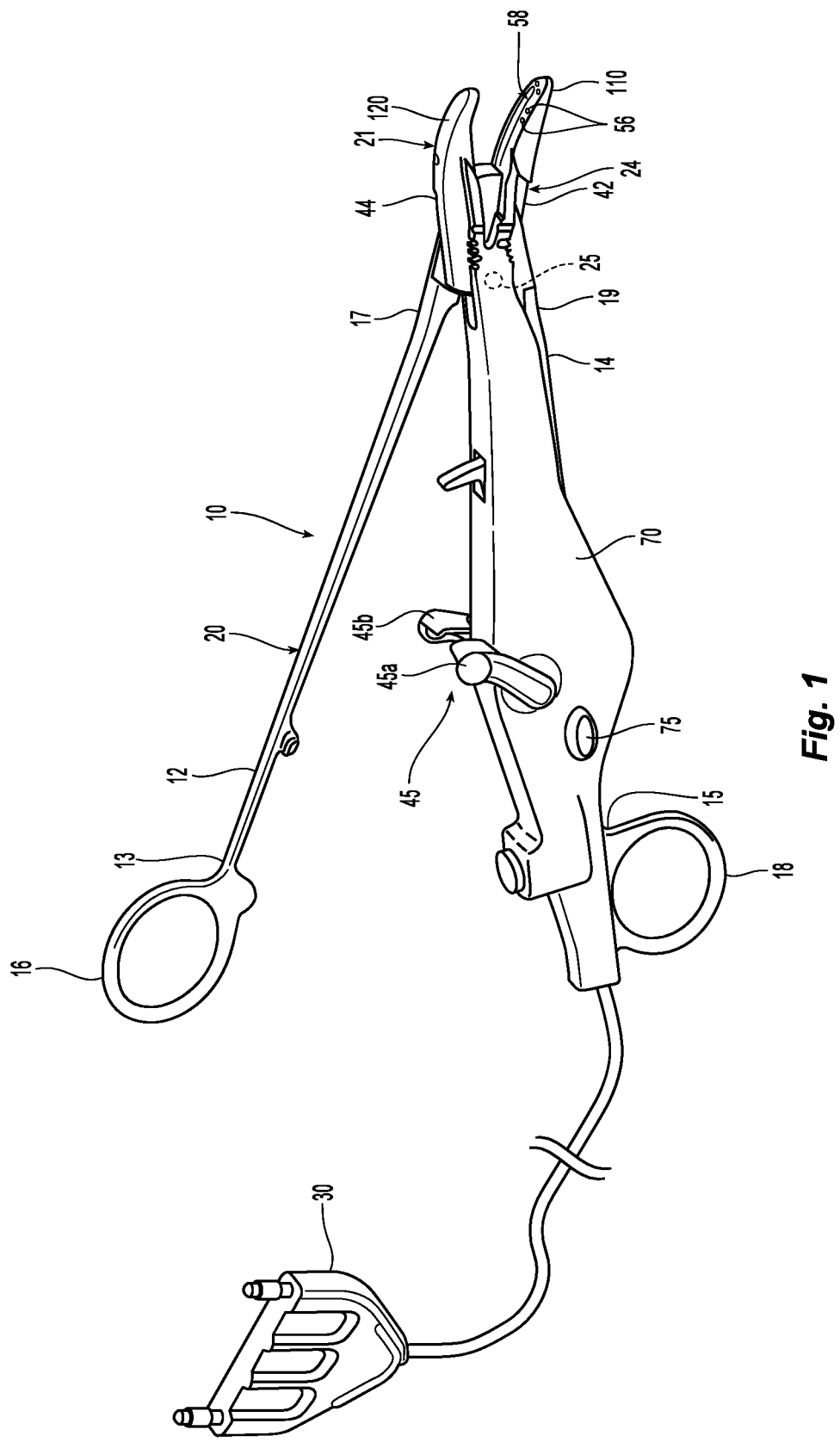
FIG. 1 is a perspective view of an open electrosurgical forceps according to an embodiment of the present disclosure including a disposable housing, a disposable electrode assembly and a trigger assembly.
Figure 2:
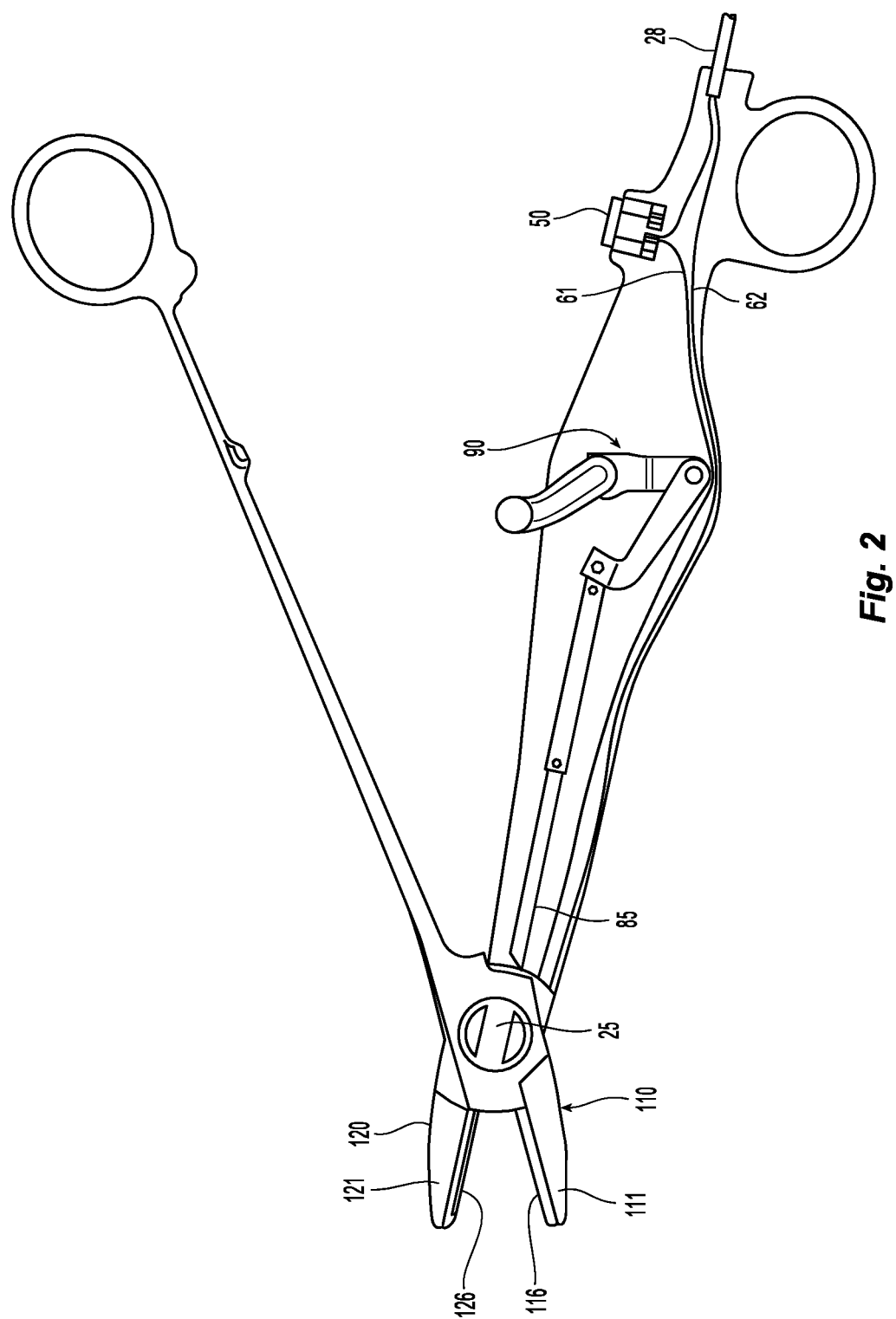
FIG. 2 is internal side view of the forceps of FIG. 1 with a trigger of the trigger assembly shown in an unactuated position.
Figure 3:
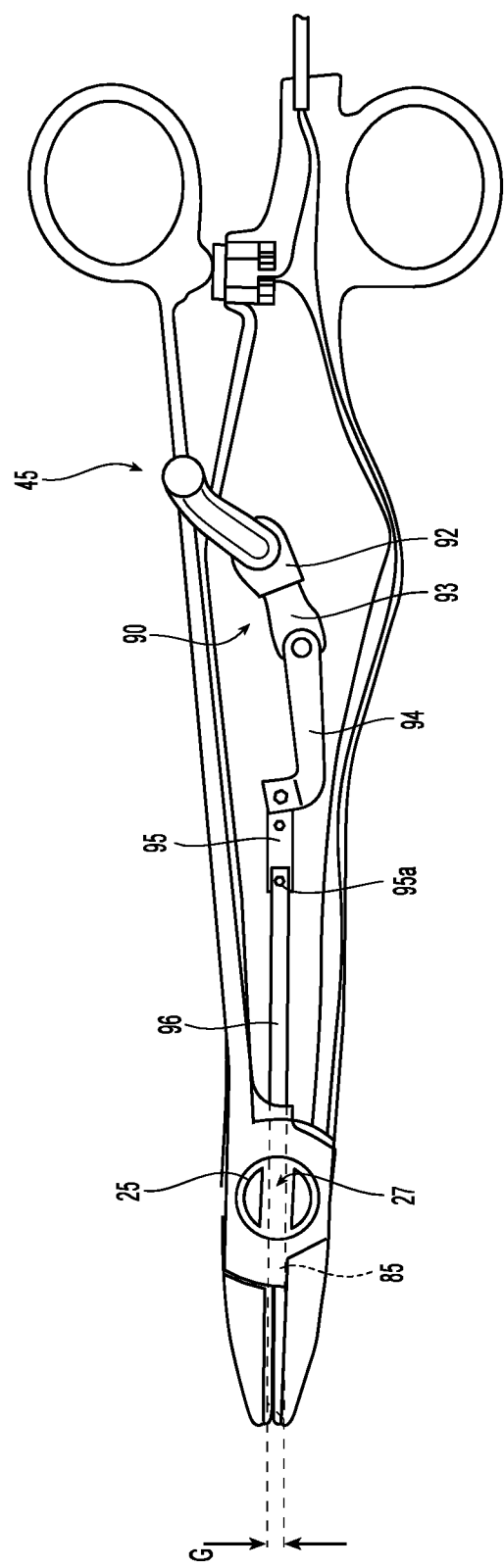
FIG. 3 is internal side view of the forceps of FIG. 1 with the trigger shown in an actuated position.

Referring initially to FIGS. 1-3, a bipolar forceps 10 for use with open surgical procedures includes a mechanical forceps 20 having an end effector 24 and a disposable electrode assembly 21. The various mechanisms and features described herein may equally relate to an endoscopic forceps (not shown). Bipolar forceps 20 includes first and second elongated shaft members 12 and 14. Elongated shaft member 12 includes proximal and distal end portions 13 and 17, respectively, and elongated shaft member 14 includes proximal and distal end portions 15 and 19, respectively. Handle members 16 and 18 are disposed at proximal end portions 13, 15 of shaft members 12, 14, respectively, and are configured to allow a user to effect movement of at least one of the shaft members 12 and 14 relative to the other. The end effector 24 includes opposing jaw members 42, 44 that extend from the distal end portions 17 and 19 of shaft members 12 and 14, respectively. The jaw members 42, 44 are movable relative to each other in response to movement of shaft members 12, 14.

Shaft members 12 and 14 are affixed to one another about a pivot 25 (FIG. 2) such that movement of shaft members 12, 14, imparts movement of the jaw members 42, 44 from an open configuration (FIG. 2) wherein the jaw members 44, 42 are disposed in spaced relation relative to one another to a clamping or closed configuration (FIG. 3) wherein the jaw members 42, 44 cooperate to grasp tissue therebetween. In embodiments, the forceps 10 may be configured such that movement of one or both of the shaft members 12, 14 causes only one of the jaw members to move with respect to the other jaw member. This is particularly noted with respect to endoscopic forceps (not shown) which may include jaw members that move in a unilateral fashion.

Disposable electrode assembly 21 is configured to releasably couple to mechanical forceps 20 and is operably coupled to a housing 70 having a pair of housing halves configured to matingly engage and releasably encompass at least a portion of shaft member 14. Disposable electrode assembly 21 includes opposing electrodes 110 and 120 that are configured to releasably couple to respective corresponding jaw members 24 and 21. Housing 70 also serves to at least partially house a knife 85 having a sharpened distal cutting edge and a knife actuation mechanism or trigger assembly 90 configured to effect advancement of the knife 85 through a knife channel 58 (FIG. 1) defined in one or both electrodes 110, 120 to transect tissue, as further detailed below. One or more push buttons 75 is disposed on housing 70 and is accessible to allow a user to actuate the button 75 to release the mechanical coupling of housing 70 and shaft member 14.

As shown in FIGS. 2 and 3, a pair of wires 61 and 62 are electrically connected to the electrodes 120 and 110, respectively, and are bundled to form a cable 28 that extends through housing 70 and terminates at a terminal connector 30 configured to mechanically and electrically couple to a suitable energy source, such as an electrosurgical generator (not shown). In embodiments, wire 61 may be configured to extend through an activation switch 50 that, upon actuation thereof, energy is supplied to the electrodes 110 and 120. Other types of activation switches 50 are also contemplated which, upon actuation thereof, send an electrical signal to the generator to supply energy to the opposing electrodes 110 and 120. Examples of electrosurgical generators include the LIGASURE® Vessel Sealing Generator and the ForceTriad® Generator sold by Covidien. In some embodiments, a suitable energy source may be a battery (not shown) supported by the housing 70 and electrically connected to the electrodes 110 and 120.

As shown in FIG. 2, electrode 120 includes an electrically conductive sealing surface 126 configured to conduct electrosurgical energy therethrough and an electrically insulative substrate 121 that serves to electrically insulate sealing surface 126 from jaw member 44. Electrode 110 includes an electrically conductive sealing surface 116 configured to conduct electrosurgical energy therethrough and an electrically insulative substrate 111 attached thereto.

While jaw members 42, 44 are in an open configuration, the electrodes 120 and 110 may be slid between opposing jaw members 44 and 42 to couple electrodes 120 and 110 with jaw member 44 and 42, respectively. Housing 70 may then be coupled about at least a portion of shaft member 14.

To electrically control the end effector 24, activation button 50 is operable by a user to initiate and terminate the delivery of electrosurgical energy to end effector 24. During use, depressing activation button 50 initiates the delivery of electrosurgical energy to the opposing electrodes 110, 120 of the end effector 24 to effect a tissue seal. In some embodiments, delivery of electrosurgical energy to end effector 24 may also be terminated by the electrosurgical generator based on any suitable parameters, e.g., sensed tissue properties, time parameters, sensed energy properties, etc.

Once a tissue seal is established, the knife 85 may be advanced through the knife channel 58 to transect the sealed tissue, as detailed below. However, in some embodiments, knife 85 may be advanced through the knife channel 58 before, during, or after tissue sealing. In some embodiments, a knife lockout mechanism (not shown) is provided to prevent extension of the knife 85 into the knife channel 58 when the jaw members 42, 44 are in the open configuration, thus preventing accidental or premature transection of tissue, as described below.

With reference to FIGS. 3-6B, the knife actuation mechanism or trigger assembly 90 is operably associated with a trigger 45 (FIG. 1) having opposing trigger handles 45a, 45b extending from opposing sides of housing 70. Upon actuation of trigger handles 45a, 45b, the trigger assembly 90 responds utilizing a series of inter-cooperating elements to actuate the knife 85 through the knife channel 58 to sever tissue grasped between jaw members 42, 44. The trigger assembly 90 includes a first link 92 that couples to the trigger handles 45a and 45b via pivot 92a. A second link 93 is slidingly or telescopically received within link 92 (or vice versa) and is movable from a compressed configuration to an extended configuration. A biasing member or spring 97 biases the two links 92 and 93 in the extended configuration. A third link 94 is coupled to an opposite end of link 93 via pivot 93a, which, in turn, couples to a fourth link 95 via pivot 94a that ultimately connects to the knife 85 via link 96. Link 96 connects to the knife 85 via pivot 95a.

As best shown in FIGS. 4A, 5A and 6A which depict the sequential movement of the various links of the trigger assembly 90 upon movement of the trigger 45 to deploy the knife 85 to cut tissue, links 92 and 93 allow the trigger assembly 90 to rotate around a reduced arc while advancing the knife 85. More particularly, as mentioned above, link 92 is dimensioned to slidingly receive link 93 (or vice versa). In a first unactuated position, links 92 and 93 are extended to a length X1 due to the bias of the spring 97 between links 92 and 93 and a minimum angle is disposed between links 92, 93 (in combination) and link 94. A compression rail 91 serves to reduce movement of the inter-cooperating links 92, 93 during actuation. Upon rotation of the trigger 45 towards a 90 degree angle, link 93 slides within link 92 against the bias of spring 97 to a compressed configuration having a length X2. This reduces the arc of rotation of the two links 92 and 93 which allows for the design of a smaller housing 70, i.e., the length X2 is also the maximum allowable distance between pivot 92a and compression rail 91. The two links 92 and 93 are normal to the fourth link 94 when disposed in a fully compressed configuration. Continued rotation of the trigger 45 towards a greater than 90 degrees angle works to advance the knife 85 while the two links 92 and 93 are urged back towards an extended configuration having a length X1 under the bias of spring 97.

A biasing member (e.g., a torsion spring not shown) may be disposed between the first link 92 and the handle member 45 which is operably coupled at one end to a portion of the first link 92 and at the other end to a suitable mechanical interface within the housing 70 that stabilizes the biasing member during use of the knife trigger assembly 90. The biasing member serves to bias the trigger 45 such that subsequent to actuation of the knife 85 through the knife channel 58, handle member 45 is biased to return to an unactuated position thereby retracting the knife 85 proximally.

With reference to FIG. 2, pivot 25 defines a longitudinal passageway 27 therebetween to allow the knife 85 to reciprocate therethrough. Movement of shaft members 12, 14 relative to each other causes rotational movement of pivot 25 and the passageway 27 from a first position wherein the jaw members 42 and 44 are spaced relative to one another and knife 85 is prevented from passing therethrough to a second position wherein the jaw members 42 and 44 are closer to one another and the knife 85 is free to pass therethrough.

A knife guide (not shown) may be supported within the housing 70 between the end effector 24 and the trigger assembly 90 and extends through passageway 27. Knife guide may include one or more suitable mechanical features (e.g., protrusions) that interface with corresponding suitable mechanical features disposed on shaft member 14 to provide location control, e.g., lateral support, to the knife 85 during translation thereof thereby ensuring proper alignment of the knife 85 as the knife 85 enters the knife channel 58 defined in electrodes 110, 120.

The tissue seal thickness and tissue seal effectiveness may be influenced by the pressure applied to tissue between jaw members 44, 42 and the gap distance between the opposing electrodes 110 and 120 (FIG. 5) during tissue sealing. In the second, closed position, a separation or gap distance "G" may be maintained between the sealing surfaces 116, 126 by one or more stop members 56 disposed on one or both of sealing surfaces 116, 126. The stop members 56 contact the sealing surface on the opposing jaw member and prohibit further approximation of the sealing surfaces 116, 126. In some embodiments, to provide an effective tissue seal, an appropriate gap distance of about 0.001 inches to about 0.010 inches and, desirably, between about 0.002 and about 0.006 inches may be provided. In some embodiments, the stop members 56 are constructed of an electrically non-conductive plastic or other material molded onto the sealing surfaces 116, 126, e.g., by a process such as overmolding or injection molding. In other embodiments, the stop members 56 are constructed of a heat-resistant ceramic deposited onto sealing surfaces 116, 126.

As mentioned above, the jaw members 42, 44 may be moved from the open configuration of FIGS. 1 and 2 to the closed configuration depicted in FIG. 3. As the shaft members 12, 14 pivot about pivot 25, shaft member 12 engages activation button 50 to initiate delivery of electrosurgical energy to end effector 24 to seal tissue between the jaw members 42 and 44. Once tissue is sealed, handle 45 may be selectively actuated to advance the knife 85 distally through knife channel 58. More specifically, as handle 45 rotates in the general proximal direction, the first and second links 92, 93 impart a rotational force on third link 94, thereby causing third link 94 to rotate about pivot pin 93a causing fourth link 95 to translate distally to advance knife 85 into the knife channel 58.

As indicated above, the initial position of the handle 45 is actively maintained by the influence of a biasing member (not shown) on the trigger 45. Moreover, the rotational arc of the combination of links 92, 93 and 94 is reduced by virtue of the sliding relationship of links 92 and 93 during actuation. This reduces the size of the housing 70 need to support the actuation mechanism 90.

The above-detailed aspects and features of the present disclosure may be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 7:
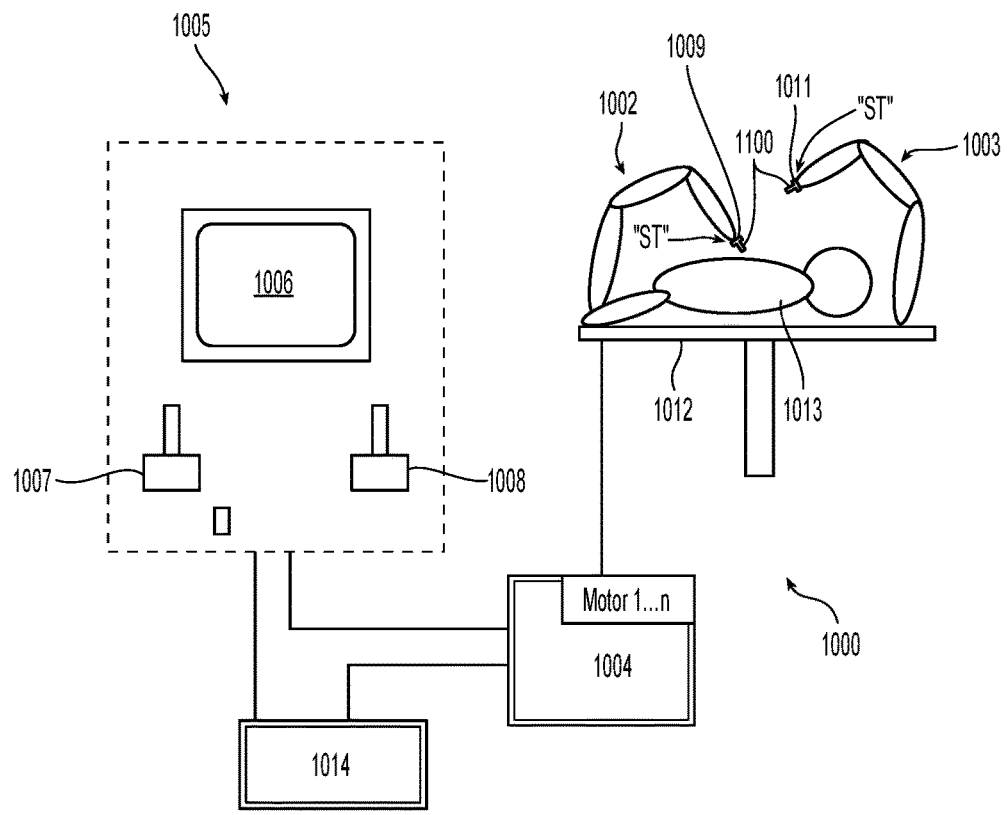
FIG. 7 is a schematic illustration of a robotic surgical system configured for use in conjunction with aspects and features of the present disclosure.

Turning to FIG. 7, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A bipolar forceps, comprising:
   at least one shaft member including a housing disposed thereon, the housing defining a cavity therein;
   an end effector assembly attached at a distal end of the at least one shaft, the end effector assembly including first and second jaw members, at least one of the first and second jaw members movable relative to the other of the first and second jaw members about a pivot from a spaced apart position to a position closer to the other of the first and second jaw members, at least one of the first and second jaw members including a knife channel defined therein configured to receive a knife therethrough;
   a trigger assembly at least partially disposed within the cavity including a trigger and a first link disposed within the housing and pivotably coupled at one end to the trigger and slidingly engaged to a second link at a second end, the second link disposed within the housing and including a first end at least partially telescopically slidable relative to the first link upon actuation of the trigger through a range of motion and a second end pivotably coupled to a third link, the third link disposed within the housing and coupled to the knife such that the actuation of the trigger translates the knife through the knife channel through the range of motion of the trigger.

2. The bipolar forceps according to claim 1, wherein the first and second links are transitionable through the range of motion of the trigger from an extended configuration wherein the first and second links combine to define a first length to a compressed configuration wherein the first and second links combine to define a second length, the second length being shorter than the first length.

3. The bipolar forceps according to claim 2, further comprising a biasing member disposed within at least one of the first and second links and configured to bias the first and second links in the extended configuration.

4. The bipolar forceps according to claim 1, wherein the second link is telescopically received within the first link.

5. The bipolar forceps according to claim 2, wherein the first and second links transition between the extended and compressed configurations through the range of motion of the trigger during the actuation of the trigger and a release of the trigger.

6. The bipolar forceps according to claim 2, wherein the first and second links are normal to the third link when disposed in the compressed configuration.

7. The bipolar forceps according to claim 1, wherein the pivot defines a longitudinal slot therethrough and the knife is configured to move within the longitudinal slot upon translation thereof.

8. A bipolar forceps, comprising:
   first and second shaft members, at least one of the first and second shaft members configured to support a housing defining a cavity therein;
   a first jaw member attached to the first shaft member and a second jaw member attached to the second shaft member, the first and second jaw members movable relative to one another about a pivot from a spaced apart position to a position closer to one another, at least one of the first and second jaw members including a knife channel defined therein configured to receive a knife therethrough;
   a trigger assembly at least partially disposed within the cavity including a trigger and a first link disposed within the housing and pivotably coupled at one end to the trigger and slidingly engaged to a second link at a second end, the second link disposed within the housing and including a first end at least partially telescopically slidable relative to the first link upon actuation of the trigger through a range of motion and a second end pivotably coupled to a third link, the third link disposed within the housing and coupled to the knife such that the actuation of the trigger translates the knife through the knife channel through the range of motion of the trigger.

9. The bipolar forceps according to claim 8, wherein the first and second links are transitionable through the range of motion of the trigger from an extended configuration wherein the first and second links combine to define a first length to a compressed configuration wherein the first and second links combine to define a second length, the second length being shorter than the first length.

10. The bipolar forceps according to claim 9, further comprising a biasing member disposed within at least one of the first and second links and configured to bias the first and second links in the extended configuration.

11. The bipolar forceps according to claim 8, wherein the second link is telescopically received within the first link.

12. The bipolar forceps according to claim 9, wherein the first and second links transition between the extended and compressed configurations through the range of motion of the trigger during the actuation of the trigger and a release of the trigger.

13. The bipolar forceps according to claim 9, wherein the first and second links are normal to the third link when disposed in the compressed configuration.

14. The bipolar forceps according to claim 8, wherein the pivot defines a longitudinal slot therethrough and the knife is configured to advance through the longitudinal slot upon translation thereof.

* * * * *